US00PP26448P2

(12) United States Plant Patent
Hurd

(10) Patent No.: US PP26,448 P2
(45) Date of Patent: Mar. 1, 2016

(54) ***SEDUM* PLANT NAMED 'LEMONJADE'**

(50) Latin Name: ***Sedum* hybrid**
Varietal Denomination: Lemonjade

(71) Applicant: Kevin A. Hurd, Austin, TX (US)

(72) Inventor: Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 115 days.

(21) Appl. No.: 14/120,515

(22) Filed: May 28, 2014

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

UPOV hit for *Sedum* plant named 'Lemonjade', CA PBR 14-8184, published Apr. 30, 2014.*

* cited by examiner

*Primary Examiner* — Anne Grunberg

(57) ABSTRACT

The new and distinct cultivar of perennial *Sedum* plant named 'Lemonjade' is characterized by tight-forming compact clumps, flower stems that remain erect in the center of the plant throughout the growing season, medium-sized blue-green foliage and numerous pale yellow flowers clustered on huge heads completely covering the plant.

1 Drawing Sheet

Botanical designation: *Sedum* hybrid.
Cultivar denomination: 'Lemonjade'.

BACKGROUND OF THE INVENTION

The present invention relates to a new and distinct cultivar of *Sedum* plant, botanically known as *Sedum* and hereinafter referred to by the cultivar name 'Lemonjade'. There are over 300 recognized species of the genus *Sedum*.

The new *Sedum* plant is a selection of a planned breeding program conducted by the inventor, Kevin A. Hurd at a wholesale perennial nursery in Zeeland, Mich., USA.

The new *Sedum* plant originated from an open pollinated batch of seeds collected on Nov. 5, 2008 with 'Sheila McQueen' (not patented) as the female or pod parent. The cross was not controlled and therefore the pollen parent is unknown. Pollen may have come from many other cultivars or seedlings within the breeding area. *Sedum* 'Lemonjade' was discovered and originally selected in the summer of 2009 by the inventor as a single plant from among thousands of plants from this lineage and hundreds of other crosses and collections performed. The selected clone was originally given the breeder code of K8-53-03 and was selected for it strong, healthy growth and compact non-drooping form together with the large heads of unique flower color.

Asexual reproduction of *Sedum* 'Lemonjade' by vegetative cuttings at a wholesale perennial nursery in Zeeland, Mich., USA since the summer of 2010, has shown that the unique features of this new *Sedum* plant are stable and reproduced true to type in successive generations.

SUMMARY OF THE INVENTION

Plants of *Sedum* 'Lemonjade' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Lemonjade'. The following characteristics in combination distinguish 'Lemonjade' as a new and distinct *Sedum* plant unique from all other *Sedum* plants known to the inventor:

1. Tight-forming compact clumps.
2. Stems remain erect in the center of the plant throughout the growing season.
3. Medium-sized, blue-green foliage.
4. Numerous pale-yellow flowers clustered on huge heads completely covering the plant.

In comparison to the female parent, *Sedum* 'Sheila McQueen', the new plant forms a taller clump, the flowers of 'Lemonjade' are pale-yellow in effect while those of 'Sheila McQueen' are reddish pink, and the foliage of 'Lemonjade' is blue-green while the foliage of 'Sheila McQueen' is brighter yellowish-green. Compared to the new plant, *Sedum* 'Pure Joy' U.S. Plant Pat. No. 24,194 is shorter with less broad heads of flowers that are pink bi-color and more narrow foliage with margins that have larger serration and develop magenta tinting.

Compared to *Sedum* 'Yellow Xenox' U.S. Plant Pat. No. 21,528 the new plant has more flowers that have a cream effect with less reddish pigment in the flowers as the flowers age and the width of the plant in flower is much greater.

*Sedum* 'Strawberries and Cream' (not patented) has dark purple tinted foliage on reddish stems and the pink flower buds produce green-centered white flowers compared to the new plant.

Compared to 'Lemonjade', *Sedum* 'Cream Yellow' (not patented) is much narrower in habit, but has cream-colored flowers that emanate from greenish yellow buds.

Compared to *Sedum* 'Stardust' (not patented), the new plant has much larger flower heads that are more cream effect than the white of 'Stardust', and the flowers of the new plant have shorter and broader sepals.

One other major difference between all the above cultivars and the new plant *Sedum* 'Lemonjade' is the new plant has not been observed to produce stamens.

BRIEF DESCRIPTION OF THE PHOTOGRAPH

The photograph of the new plant demonstrates the unique traits and the overall appearance of *Sedum* 'Lemonjade'.

The colors are as accurate as reasonably possible with color reproductions of this type. Variations in ambient light spectrum, source and direction may cause the appearance of minor variation in color. The plants used in the photograph were two-year old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

The following is a detailed description of two year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2001 edition of The Royal Horticultural Society Colour Chart except where general color dictionary terms are used.

Botanical designation: *Sedum* hybrid.

Cultivar denomination: 'Lemonjade'.

Parentage: 'Sheila McQueen' (not patented) female, or seed, parent; male or pollen parent unknown.

Asexual propagation: Stem cuttings and division.

Time to initiate roots: About two weeks.

Time to finish a 3.7 liter flowering container: About three months in the summer from a rooted 2.5 cm plug.

Root description: Thick, fleshy; freely branching; creamy white to light tan in color.

Plant habit: Winter-hardy herbaceous perennial; upright mounded; stems stiff and upright arising from a dense base; flower heads freely branching; dense and full, not opening in center later in the season.

Growth rate: Moderately vigorous.

Plant size: About 40.0 cm tall and 54 cm wide in full flower.

Main stems: Glaucous; about 22 per plant; diameter at base about 6.0 mm, about 20 cm long from base to initial branches; maintaining foliage in about the upper two thirds of stem at flowering time; internodes average about 0.8 cm.

Main stem color: Base underneath glaucous bloom nearest RHS 139B, with glaucous bloom more green than RHS 122B and more blue than RHS N138C.

Lateral branches: Glaucous; about 3.0 mm diameter for first level branching and about 5.0 cm long.

Lateral branch color: Nearest RHS 136D.

Foliage: Opposite, simple; ovate; smooth, glabrous, glaucous; sessile; thick, fleshy and succulent; apex bluntly acute; base rounded; margin irregularly and shallowly dentate, primarily in distal one half; to about 8.0 cm long and 4.0 cm across, average about 5.0 cm long and 2.5 cm across decreasing in size distally.

Foliage color:

*Developing leaves.*—Adaxial surface nearest RHS 138D, abaxial surface nearest RHS 138D.

*Fully developed leaves at flowering time.*—Adaxial surface nearest RHS N138A, abaxial surface nearest RHS N138C.

Venation: Pinnate; color same as surrounding leaf tissue on both surfaces.

Flower: Small, rotate, upright, actinomophic; in terminal compound cymes; freely flowering habit with about 10,000 flower buds and flowers per plant covering nearly the entire surface; about 6.0 mm across and 9.0 mm long.

Fragrance: Faint, sweet.

Flowering season: Beginning late August to late September in Zeeland, Mich.; able to be forced to flower in greenhouse out of season with about 2 months of growth following 9 weeks of vernalization.

Longevity: Flower cymes remain effective for about three weeks on the plant and one week as cut flowers; individual flowers persistent.

Flower buds about one day prior to opening: Broadly elliptic; apex broadly acute; base rounded; about 2.5 mm diameter and 3.5 mm long.

Flower bud color: Nearest RHS 157C.

Inflorescence: About 20 cm tall from first branch and 16 cm across; about 450 flowers per inflorescence.

Petals: Typically five, broadly-lanceolate; acute apex, base fused, margin entire, glabrous; typically 1.0 mm long and less than 0.5 mm across, rarely about 3.5 mm long and 2.0 mm across.

Petal color: Nearest RHS 155D on both adaxial and abaxial surfaces.

Sepals: Typically five, lanceolate; entire; glabrous; glaucous; acute apex, fused at the base margin; campanulate; about 2.5 mm long and about 1.0 mm wide at fused base.

Sepal color: Nearest RHS N138C both adaxial and abaxial surfaces.

Peduncles: Glaucous, glabrous; strong and stiff, yet flexible; freely branching; angle erect in center to nearly 45 degrees from perpendicular for perimeter peduncles; about 20 cm long and 5.0 mm diameter.

Peduncle color: Nearest RHS 138B.

Pedicels: Glaucous, glabrous; strong and stiff, yet flexible; about 3.0 mm long and 0.8 mm diameter.

Pedicel color: Between RHS 138A and RHS 138B.

Androecium: Have not observed under present growing conditions; Stamens, filaments, anthers and pollen not observed.

Gynoecium: Typically four, rarely three; cylindrical, conic in distal one third.

*Style.*—About 1.5 mm long and 0.5 mm diameter at point of attachment to ovary; glabrous; color beginning nearest RHS N155B and darkening to nearest RHS 186C at petal dehiscence.

*Stigma.*—Minute; color beginning nearest RHS N155B and darkening to nearest RHS 186C at petal dehiscence.

*Ovary.*—Nearly cylindrical, tapering at apex to style; about 4.0 mm long and 3.0 mm diameter; color nearest RHS 157C.

Seed and fruit: Have not yet been observed.

Disease and pest resistance: Plants of the new *Sedum* 'Lemonjade' grow best with good drainage, full sun and moderate to low fertility. 'Lemonjade' is cold hardy from USDA zones 4 to 9 and has tolerated temperatures of at least 35 degrees C. 'Lemonjade' tolerates heavy rains and wind and does not tend to develop an open center later in the season as many other *Sedum* cultivars do. *Sedum* 'Lemonjade' is not prone to rabbit damage. Other pest and disease resistance and tolerance outside that normal for *Sedum* is not known.

It is claimed:

1. The new and distinct perennial *Sedum* plant named 'Lemonjade' as herein described and illustrated useful for landscaping as a specimen plant, en masse or as a cut flower.

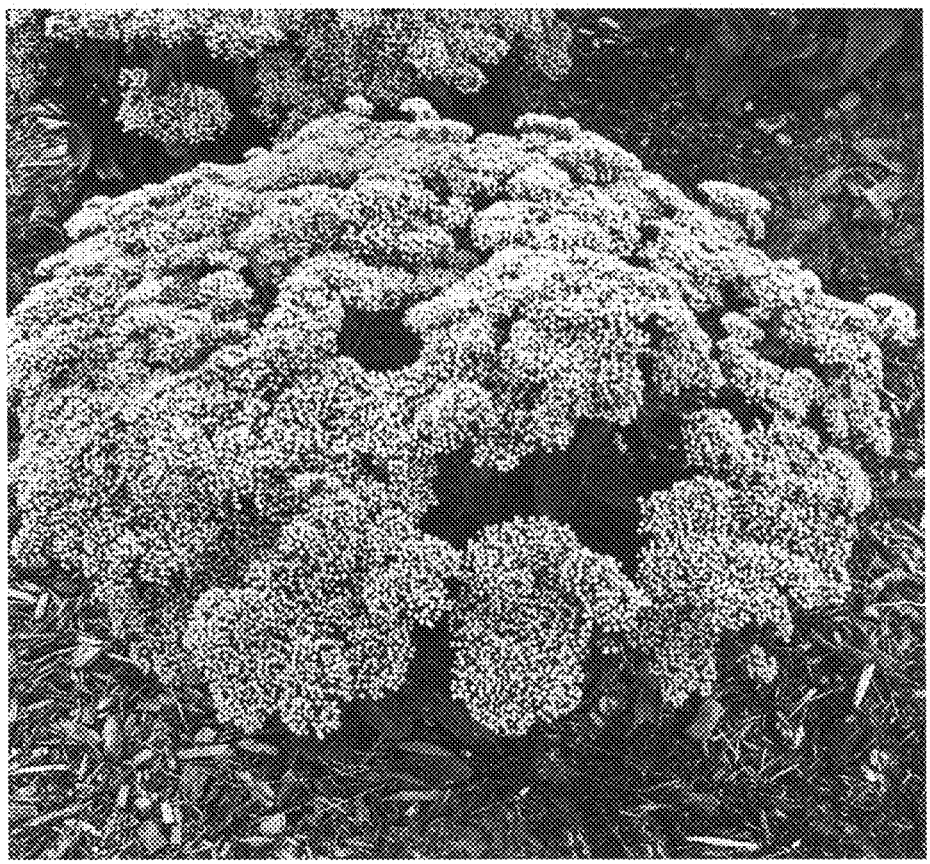

* * * * *